United States Patent
Krämer et al.

(10) Patent No.: US 10,414,985 B2
(45) Date of Patent: Sep. 17, 2019

(54) HEPTAPHOSPHORUS-DERIVED COMPOUNDS AS FLAME RETARDANTS

(71) Applicant: BASF SE, Ludwigshafen (DE)

(72) Inventors: Roland H. Krämer, Mannheim (DE); Peter Deglmann, Mannheim (DE); Alexander König, Bruchsal (DE); Rebekka Von Benten, Ludwigshafen (DE); Andrea Eisenhardt, Vechta (DE); Sindhu Menon, Pudong (CN); Frank Reuter, Undenheim (DE); Hansjörg Grützmacher, Dielsdorf (CH); Aaron Tondreau, Zürich (CH)

(73) Assignee: BASF SE (DE)

( * ) Notice: Subject to any disclaimer, the term of this patent is extended or adjusted under 35 U.S.C. 154(b) by 80 days.

(21) Appl. No.: 15/128,775

(22) PCT Filed: Mar. 24, 2015

(86) PCT No.: PCT/EP2015/056197
§ 371 (c)(1),
(2) Date: Sep. 23, 2016

(87) PCT Pub. No.: WO2015/144667
PCT Pub. Date: Oct. 1, 2015

(65) Prior Publication Data
US 2018/0216008 A1 Aug. 2, 2018

(30) Foreign Application Priority Data
Mar. 27, 2014 (EP) .................... 14161894

(51) Int. Cl.
| | |
|---|---|
| C09K 21/12 | (2006.01) |
| C07F 9/6568 | (2006.01) |
| C08K 3/32 | (2006.01) |
| C08K 5/50 | (2006.01) |
| C01B 25/06 | (2006.01) |
| C08K 5/3492 | (2006.01) |
| C08K 5/54 | (2006.01) |
| C07F 9/50 | (2006.01) |
| C08K 5/3437 | (2006.01) |
| C08K 5/5425 | (2006.01) |
| C09K 21/10 | (2006.01) |

(52) U.S. Cl.
CPC ............. *C09K 21/12* (2013.01); *C01B 25/06* (2013.01); *C07F 9/504* (2013.01); *C07F 9/6568* (2013.01); *C08K 3/32* (2013.01); *C08K 5/3437* (2013.01); *C08K 5/34922* (2013.01); *C08K 5/50* (2013.01); *C08K 5/5406* (2013.01); *C08K 5/5425* (2013.01); *C09K 21/10* (2013.01)

(58) Field of Classification Search
None
See application file for complete search history.

(56) References Cited

U.S. PATENT DOCUMENTS

| | | | | |
|---|---|---|---|---|
| 2,486,658 | A | * 11/1949 | Kosolapoff | ............. C07F 9/098 558/128 |
| 3,030,331 | A | 4/1962 | Goldberg | |
| 3,169,121 | A | 2/1965 | Goldberg | |
| 4,130,458 | A | 12/1978 | Moore et al. | |
| 4,223,071 | A | 9/1980 | Boyer et al. | |
| 4,263,201 | A | 4/1981 | Mark et al. | |
| 4,286,083 | A | 8/1981 | Kochanowski | |
| 4,552,704 | A | 11/1985 | Mark | |
| 5,210,268 | A | 5/1993 | Fukuoka et al. | |
| 5,606,007 | A | 2/1997 | Sakashita et al. | |
| 6,660,787 | B2 | 12/2003 | Mahood et al. | |
| 6,727,302 | B2 | 4/2004 | Goossens et al. | |
| 6,730,720 | B2 | 5/2004 | Gohr et al. | |
| 8,519,035 | B2 | 8/2013 | Tishkov et al. | |
| 9,129,767 | B2 | 9/2015 | Brignoli et al. | |
| 2013/0338272 | A1 | 12/2013 | Krämer et al. | |
| 2013/0338290 | A1 | 12/2013 | Krämer et al. | |
| 2014/0080949 | A1 | 3/2014 | Roth et al. | |

FOREIGN PATENT DOCUMENTS

| | | |
|---|---|---|
| CN | 102482445 A | 5/2012 |
| DE | 19638924 A1 | 4/1997 |
| DE | 102010040632 A1 | 3/2011 |
| GB | 2306478 A | 5/1997 |
| JP | 2010-538139 A | 12/2010 |

OTHER PUBLICATIONS

Knapp et al. (Inorg. Chem. 2011, 50, 4021-4028).*
Charles, S., et al., "Tetraalkylammonium Salts as Stereospecific Alkylating Agents for Highly Nucleophilic Polyphosphide Zintl Anions: Preparation of [RP$_7$W(CO)$_3$]$^{2-}$, [R$_2$P$_7$]$^-$, and R$_2$R'P$_7$ Compounds from R$_4$N$^+$Reagents", Journal of the American Chemical Society, vol. 117, No. 19, (1995), pp. 5303-5311.
Milyukov, V., et al., "Trisodium heptaphosphide in reactions with alkyl and aryl tosylates", Russian Chemical Bulletin, International Edition, vol. 56, No. 2, (2007), 298-303.
International Search Report for PCT/EP2015/056197 dated Sep. 23, 2015.

* cited by examiner

*Primary Examiner* — Robert T Butcher
(74) *Attorney, Agent, or Firm* — Drinker Biddle & Reath LLP

(57) ABSTRACT

The invention relates to flame retardant compositions comprising heptaphosphorus-derived compounds and to novel heptaphosphorus-derived compounds.
These heptaphosphorus-derived compounds are especially useful for the manufacture of flame retardant compositions based on thermoplastic polymers, especially polyolefin homo- and copolymers, polycondensates, such as polyamides, or polyesters and duroplastic polymers, such as the ones based on polyepoxides.

16 Claims, 2 Drawing Sheets

Figure 1

Digital photograph of an epoxy plate containing tris-1-(1,3-diphenyl-3-oxo-propyl)heptaphosphine (Example 2) in a mass fraction of 8.0 % w/w. The BASF logo is placed behind the specimen in order to demonstrate the clarity of the material:

Figure 2

Digital photograph of an epoxy plate containing tris(3-oxo-1-phenyl-propyl)-heptaphosphine (Example 5) in a mass fraction of 8.0 % w/w. The BASF logo is placed behind the specimen in order to demonstrate the clarity of the material:

Figure 3

Digital photograph of an epoxy plate containing red phosphorus (Example 5e)).

HEPTAPHOSPHORUS-DERIVED COMPOUNDS AS FLAME RETARDANTS

CROSS-REFERENCE TO RELATED APPLICATIONS

This application is a national stage application (under 35 U.S.C. § 371) of PCT/EP2015/056197, filed Mar. 24, 2015, which claims benefit of European Application No. 14161894.2, filed Mar. 27, 2014, both of which are incorporated herein by reference in their entirety.

The present invention relates to novel heptaphosphorus-derived compounds and their use in flame retardant polymer compositions. The invention also relates to flame retardant composition comprising these heptaphosphorus-derived compounds.

These heptaphosphorus-derived compounds are especially useful for the manufacture of flame retardant compositions based on thermoplastic polymers, especially polyolefin homo- and copolymers, polycondensates, such as polyamides or polyesters, and duroplastic polymers, such as the ones based on polyepoxides.

Flame retardants are added to polymeric materials (synthetic or natural) to enhance the flame retardant properties of the polymers. Depending on their composition, flame retardants may act in the solid, liquid or gas phase either chemically, e.g. as a spumescent by liberation of nitrogen, and/or physically, e.g. by producing a foam coverage. Flame retardants interfere during a particular stage of the combustion process, e.g. during heating, decomposition, ignition or flame spread.

Many flame retardants are known, such as the ones based on nitrogen containing compounds, e.g. melamine cyanurate, melamine phosphate, melamine polyphosphate, ammonium polyphosphate, melamine ammonium phosphate, melamine ammonium polyphosphate, melamine ammonium pyrophosphate, condensation products of melamine with phosphoric acid and other reaction products of melamine with phosphoric acid.

Red phosphorus imparts an excellent effect of flame retardancy in selected polymers (PA, PU), whereas flame retardancy is insufficient in other polymers (PBT, polyolefins). The use of red phosphorus is further limited by its strong colour effect in polymer substrates, insufficient storage stability in the event that residual amounts of water are present (PBT and PU) and undesirable sedimentation in reactive resins during storage (PU).

There is still a need for flame retardant compositions with improved properties that can be used in different polymer substrates. Increased standards with regard to safety and environmental requirements result in stricter regulations. Particularly, known halogen containing flame retardants no longer match all necessary requirements. Therefore, halogen-free flame retardants or flame retardants of low halogen content are preferred, particularly in view of their better performance in terms of smoke density associated with fire. Improved thermal stability and less corrosive behaviour are further benefits of halogen free flame retardant compositions.

It has surprisingly been found that thermoplastic or duroplastic polymers with excellent flame retardant properties are prepared in the event that selected heptaphosphorus-derived ($P_7$) compounds are added to the polymer substrate.

The invention relates to a composition, particularly a flame retardant composition, which comprises
 a) A heptaphosphorus-derived ($P_7$) compound; and
 b) A polymer substrate.

The term heptaphosphorus-derived ($P_7$) compound comprises within its scope a phosphorus compound, wherein 7 phosphorus atoms form a cage structure of the heptaphosphatricyclo[$2.2.1.0^{2,6}$]heptane-type with three secondary modifiable (substitutable) phosphorus atoms. The phosphorus atoms are thus preferably arranged in a tricyclic structure to which up to 3 ligands are attached or coordinated. A registered example with this structure is $P_7H_3$, (CAS 51273-53-1). Further examples of such ligands are individual metal ions, such as zinc ions, other ionic groups known from complex or coordination chemistry, non-metal atoms with further substituents, such as triorganyl silicon groups, or organic groups, such as the ones explained below. There is a direct bond between the $P_7$ group and the metal atoms, such as zinc, non-metal atoms, such as silicon, and/or the carbon atoms of the organic groups.

According to a preferred embodiment, the heptaphosphorus-derived ($P_7$) compound is selected from the group consisting of zinc heptaphosphorus halide, triazine heptaphosphide, tris-trialkylsilyl-heptaphosphide and trialkylheptaphosphine.

Zinc heptaphosphorus halide is obtainable by reaction of zinc halide, particularly zinc chloride, with tris-trialkylsilyl-heptaphosphide, e.g. $P_7(TMS)_3$ (=tris-trimethylsilylheptaphosphide) in an organic solvent, such as THF.

$P_7(TMS)_3$ is obtainable by the method described in H. Schmidbaur, A. Bauer, *An improved preparation of tris (trimethylsilyl)heptaphosphine*, Phosphorus, Sulfur, and Silicon, 1995, Vol. 102. pp. 217-219.

Another embodiment of the invention relates to a composition, particularly a flame retardant composition, which comprises
 a) Zinc heptaphosphorus halide; and
 b) A polymer substrate.

A further embodiment relates to a composition, particularly a flame retardant composition, which comprises
 a) tris-Trialkylsilyl-heptaphosphide, particularly tris-trimethylsilylheptaphosphide; and
 b) A polymer substrate.

A triazine heptaphosphide is obtainable by known or analogous methods, e.g. by reaction of tris-trialkylsilyl-heptaphosphide, e.g. $P_7(TMS)_3$ (=tris-trimethylsilylheptaphosphide), with a suitable triazine compound, such as melamine, or the condensation product of melamine from the series melem, melam and melon.

The heptaphosphorus-derived ($P_7$) compound with melamine or the condensation product of melamine from the series melem, melam and melon is novel and also subject matter of the present invention.

Therefore, a further embodiment of the invention relates to the triazine heptaphosphide addition compound and to the preparation of that compound.

A further embodiment relates to a composition, particularly a flame retardant composition, which comprises a) a heptaphosphorus-derived ($P_7$) compound selected from the group consisting of zinc heptaphosphorus halide, triazine heptaphosphide, tris-trialkyl-silyl-heptaphosphide and trialkylheptaphosphine.

The invention particularly relates to a composition, particularly a flame retardant composition, which comprises a) a heptaphosphorus-derived ($P_7$) compound selected from the group consisting of zinc heptaphosphorus chloride, melamine heptaphosphide, tris-trimethylsilyl-heptaphosphine and trialkylheptaphosphine of the formula $$P_7(R_x)_3 \quad (I),$$

Wherein $R_x$ represents a group of the partial formula $$-CR_1R_2R_3 \quad (A),$$

Wherein
a) One of $R_1$, $R_2$ and $R_3$ represents hydrogen;
   One of $R_1$, $R_2$ and $R_3$ represents $C_1$-$C_4$-alkyl, phenyl or $C_1$-$C_4$-alkyl substituted by phenyl; and
   One of $R_1$, $R_2$ and $R_3$ represents the group of the partial formula $$-CH=CR_aR_b \quad (B),$$

Wherein
   One of $R_a$ and $R_b$ represents ($C_1$-$C_4$alkyl)$_3$silyl; and the other
   One of $R_a$ and $R_b$ represents $C_1$-$C_4$-alkyl, phenyl or $C_1$-$C_4$-alkyl substituted by phenyl; or
b) One of $R_1$, $R_2$ and $R_3$ represents hydrogen;
   One of $R_1$, $R_2$ and $R_3$ represents $C_1$-$C_4$-alkyl, phenyl or $C_1$-$C_4$-alkyl substituted by phenyl; and
   One of $R_1$, $R_2$ and $R_3$ represents the group of the partial formula $$-CH-C(=O)-R_a \quad (C),$$

Wherein
   $R_a$ represents $C_1$-$C_4$-alkyl, phenyl or $C_1$-$C_4$-alkyl substituted by phenyl; or
Wherein
c) One of $R_1$, $R_2$ and R represents hydroxy;
   One of $R_1$, $R_2$ and $R_3$ represents hydrogen; and
   One of $R_1$, $R_2$ and $R_3$ represents $C_1$-$C_4$-alkyl, phenyl or $C_1$-$C_4$-alkyl substituted by phenyl; or
d) One of $R_1$, $R_2$ and $R_3$ represents hydroxy; and
   two of $R_1$, $R_2$ and $R_3$ represent $C_1$-$C_4$-alkyl, phenyl or $C_1$-$C_4$-alkyl substituted by phenyl.

The definition $C_1$-$C_4$-alkyl comprises within its scope methyl, ethyl, n-propyl or isopropyl and n-, tert- and isobutyl.

$C_1$-$C_4$-alkyl substituted by phenyl is preferably benzyl or 1- or 2-phenylethyl.

The compositions of the invention have excellent thermal stability without undesirable colour effects and are therefore especially suited in view of their facile dispersability in thermoplastic polymers for the application in engineering thermoplastics and epoxy laminates, used for the manufacture of electrical and electronic parts and devices. Furthermore, epoxy resins comprising the inventive compounds show no or only a minor negative impact on the glass transition temperature, which is considered advantageous especially for their use in epoxy laminates for the manufacture of printed circuit boards. By using the instant flame retardant additives in thermoplastic and duroplastic resins, conventional halogen containing flame retardants and halogenated epoxy resins, antimony compounds, and inorganic fillers may largely be reduced or replaced.

A further embodiment of the invention relates to the use of a heptaphosphorus-derived ($P_7$) compound as defined above, for inducing flame retardancy in polymers.

The polymer compositions wherein heptaphosphorus ($P_7$) addition compound, as defined above, are present, attain the desirable V-0 rating, according to UL-94 (Underwriter's Laboratories Subject 94) and other excellent ratings in related test methods.

These heptaphosphorus-derived ($P_7$) compounds are preferably contained in the flame retardant compositions according to the invention in an amount from 1.0-90.0 wt.-%, preferably 2.0-50.0 wt.-%, based on the weight of the polymer substrate.

The term polymer and substrate comprises within its scope thermoplastic and duroplastic polymers and thermosets.

A list of suitable thermoplastic polymers is given below:
1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be cross linked), for example high density polymethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different and especially by the following methods:
a) Radical polymerisation (normally under high pressure and at elevated temperature).
b) Catalytic polymerisation using a catalyst that normally contains one or more than one metal of groups IVb, Vb, VIb or VIII of the Periodic Table. These metals usually have one or more than one ligand, typically oxides, halides, alkoxides, esters, ethers, amines, alkyls, alkenyls and/or aryls that may be either α- or π-bond coordinated. These metal complexes may be in the free form or fixed on substrates, typically on activated magnesium chloride, titanium (III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, and amine or silyl ether groups. These catalyst systems are usually termed Phillips, Standard Oil Indiana, Ziegler-Natta)|TNZ (DuPont), metallocene or single site catalysts (SSC).
2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).
3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinyl-cyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LOPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch;

The homopolymers and copolymers mentioned above may have a stereo structure including syndiotactic, isotactic, hem i-isotactic or atactic; where atactic polymers are preferred. Stereo block polymers are also included.

5. Polystyrene, poly(p-methylstyrene), poly(α-methylstyrene),

6. Aromatic homopolymers and copolymers derived from vinyl aromatic monomers including styrene, α-methylstyrene, all isomers of vinyl toluene, especially p-vinyl toluene, all isomers of ethyl styrene, propyl styrene, vinyl biphenyl, vinyl naphthalene, and vinyl anthracene, and mixtures thereof. Homopolymers and copolymers may have a stereo structure including syndiotactic, isotactic, hemi-isotactic or atactic; where atactic polymers are preferred. Stereo block polymers are also included;

a) Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

b) Hydrogenated aromatic polymers derived from hydrogenation of polymers mentioned under 6), especially including polycyclohexylethylene (PCHE) prepared by hydrogenating atactic polystyrene, often referred to as polyvinylcyclohexane (PVCH).

c) Hydrogenated aromatic polymers derived from hydrogenation of polymers mentioned under 6a). Homopolymers and copolymers may have a stereo structure including syndiotactic, isotactic, hemi-isotactic or atactic; where atactic polymers are preferred. Stereo block polymers are also included.

7. Graft copolymers of vinyl aromatic monomers, such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulphochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1 above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes, which contain ethylene oxide as a comonomer; polyacetals modified with thermoplastic polyurethanes, acrylates or MBS.

14. Polyphenylene oxides and sulphides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and co-polyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or co-polyamides modified with EPDM or ABS; and polyamides condensed during processing (RIM polyamide systems).

17. Polyureas, polyimides, polyamide imides, polyether imides, polyester imides, polyhydantoins and polybenzimidazoles.
18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block co-polyether esters derived from hydroxyl-terminated polyethers; and also polyesters modified with polycarbonates or MBS.
19. Polyketones,
20. Polysulphones, polyether sulphones and polyether ketones.
21. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/thermoplastic polyester elastomeres, PBT/PC/ABS or PBT/PET/PC.
22. Polycarbonates that correspond to the general formula:

Such polycarbonates are obtainable by interfacial processes or by melt processes (catalytic transesterification). The polycarbonate may be either branched or linear in structure and may include any functional substituents. Polycarbonate copolymers and polycarbonate blends are also within the scope of the invention. The term polycarbonate should be interpreted as inclusive of copolymers and blends with other thermoplastics. Methods for the manufacture of polycarbonates are known, for example, from U.S. Pat. Nos. 3,030,331; 3,169,121; 4,130,458; 4,263,201; 4,286,083; 4,552,704; 5,210,268; and 5,606,007. A combination of two or more polycarbonates of different molecular weights may be used.

Preferred are polycarbonates obtainable by reaction of a diphenol, such as bisphenol A, with a carbonate source. Examples of suitable diphenols are:

Bisphenol A bisphenol AF bisphenol AP bisphenol B bisphenol C bisphenol E bisphenol F bisphenol M bisphenol P bisphenol S bisphenol TMC bisphenol Z 4,4'-(2-norbornylidene)bis(2,6-dichlorophenol); or fluorene-9-bisphenol:

The carbonate source may be a carbonyl halide, a carbonate ester or a haloformate. Suitable carbonate halides are phosgene or carbonylbromide. Suitable carbonate esters are dialkylcarbonates, such as dimethyl- or diethylcarbonate, diphenyl carbonate, phenylalkylphenylcarbonate, such as phenyl-tolylcarbonate, dialkylcarbonates, such as dimethyl- or diethylcarbonate, di-(halophenyl)carbonates, such as di-(chlorophenyl)carbonate, di-(bromophenyl)carbonate, di-(trichlorophenyl)carbonate or di-(trichlorophenyl)carbonate, di-(alkylphenyl)carbonates, such as di-tolylcarbonate, naphthylcarbonate, dichloronaphthylcarbonate and others.

The polymer substrate mentioned above, which comprises polycarbonates or polycarbonate blends is a polycarbonate-copolymer, wherein isophthalate/terephthalate-resorcinol segments are present. Such polycarbonates are commercially available, e.g. Lexan® SLX (General Electrics Co. USA). Other polymeric substrates of component b) may additionally contain in the form as admixtures or as copolymers a wide variety of synthetic polymers including polyolefins, polystyrenes, polyesters, polyethers, polyamides, poly(meth)acrylates, thermoplastic polyurethanes, polysulphones, polyacetals and PVC, including suitable compatibilizing agents. For examthe polymer substrate may additionally contain thermoplastic polymers selected from the group of resins consisting of polyolefins, thermoplastic polyurethanes, styrene polymers and copolymers thereof. Specific embodiments include polypropylene (PP), polyethylene (PE), polyamide (PA), polybutylene terephthalate (PBT), polyethylene terephthalate (PET), glycol-modified polycyclohexylenemethylene terephthalate (PCTG), polysulphone (PSU), polymethylmethacrylate (PMMA), thermoplastic polyurethane (TPU), acrylonitrile-butadiene-styrene (ABS), acrylonitrilestyrene-acrylic ester (ASA), acrylonitrile-ethylene-propylene-styrene (AES), styrene-maleic anhydride (SMA) or high impact polystyrene (HIPS).

A preferred embodiment of the invention relates to the use of heptaphosphorus-derived ($P_7$) compound compounds in thermoplastic polymers. Preferred thermoplastic polymers include polyolefins, polyurethanes, polyamides, polyesters and polycarbonates.

Preferred is a flame retardant composition, which comprises
a) A heptaphosphorus-derived ($P_7$) compound; and
b') A thermoplastic polymer substrate.

Another preferred embodiment of the invention relates to a flame retardant composition, wherein component b) is a duroplastic polymer substrate of the polyepoxide type.

A further preferred embodiment of the invention relates to a composition, which comprises
a) A heptaphosphorus-derived ($P_7$) compound; and
b") A polyfunctional epoxide compound, and, optionally, a hardener compound.

Suitable polyfunctional epoxide compounds are epoxides, wherein at least two epoxy groups of the partial formula are present, which are attached directly to carbon, oxygen, nitrogen or sulphur atoms, and wherein q represents zero, $R_1$ and $R_3$ both represent hydrogen and $R_2$ represents hydrogen or methyl; or wherein q represents zero or 1, $R_1$ and $R_3$ together form the —$CH_2$—$CH_2$— or —$CH_2$—$CH_2$—$CH_2$— groups and $R_2$ represents hydrogen.

Suitable hardener components are, for example, amine and anhydride hardeners, such as polyamines, e.g. ethylenediamine, diethylenetriamine, triethylenetriamine, hexamethylenediamine, methanediamine, N-aminoethyl piperazine, diaminodiphenylmethane [DDM], alkyl-substituted derivatives of DDM, isophoronediamine [IPD], diaminodiphenylsulphone [DDS], 4,4'-methylenedianiline [MDA], or m-phenylenediamine [MPDA]), polyamides, alkyl/alkenyl imidazoles, dicyandiamide [DICY], 1,6-hexamethylene-bis-cyanoguanidine, or acid anhydrides, e.g. dodecenylsuccinic acid anhydride, hexahydrophthalic acid anhydride, tetrahydrophthalic acid anhydride, phthalic acid anhydride, pyromellitic acid anhydride, and derivatives thereof.

The instant invention further pertains to the use of compounds (1) in flame retardant compositions which comprise, in addition to the components defined above, optional components, such as additional flame retardants and/or further additives selected from the group consisting of tetraalkylpiperidine additives, polymer stabilizers, fillers, reinforcing agents and so-called anti-dripping agents that reduce the melt flow of thermoplastic polymers and reduce the formation of drops at higher temperatures.

The invention also relates to a process for inducing the flame retardancy in polymers, which comprises adding to a polymer substrate a combination of at least one, with at least one additional flame retardant.

Such additional flame retardants are phosphorus containing flame retardants, for example selected from the group consisting of phosphorus and/or nitrogen containing flame retardants, organohalogen containing flame retardants and inorganic flame retardants.

Phosphorus containing flame retardants are, for example, tetraphenyl resorcinol diphosphate, resorcinol phenyl phosphate oligomer (Fyrolflex® RDP, Akzo Nobel), triphenyl phosphate, bisphenol A phenylphosphate oligomer (Fyrolflex® BDP), tris(2,4-ditert-butylphenyl) phosphate, ethylenediamine diphosphate (EDAP), tetra(2,6-dimethylphenyl) resorcinol diphosphate, ammonium polyphosphate, diethyl-N,N-bis(2-hydroxyethyl)-aminomethyl phosphonate, hydroxyalkyl esters of phosphorus acids, salts of di-$C_1$-

$C_4$alkylphosphinic acids and of hypophosphoric acid ($H_3PO_2$), particularly the $Ca^{2+}$, $Zn^{2+}$, or $Al^{3+}$ salts, tetrakis(hydroxymethyl)phosphonium sulphide, triphenylphosphine, triphenyl phosphine oxide, tetraphenyldiphosphine monoxide, phosphazenes and 9,10-dihydro-9-oxa-10-phosphorylphenanthrene-10-oxide (DOPO) and its derivatives, such as 2-(9,10-dihydro-9-oxa-10-phosphaphenanthrene-10-oxide)-1,4-benzenediol.

Nitrogen generating flame retardants are, for example, isocyanurate flame retardants, such as polyisocyanurate, esters of isocyanuric acid or isocyanurates. Representative examples are hydroxyalkyl isocyanurates, such as tris-(2-hydroxyethyl)isocyanurate, tris(hydroxymethyl)isocyanurate, tris(3-hydroxy-n-proyl)isocyanurate or triglycidyl isocyanurate.

Nitrogen containing flame-retardants include further melamine-based flame-retardants. Representative examples are: melamine cyanurate, melamine borate, melamine phosphate, melamine pyrophosphate, melamine polyphosphate, melamine ammonium polyphosphate, melamine ammonium pyrophosphate, dimelamine phosphate and dimelamine pyrophosphate.

Further examples are: benzoguanamine, allantoin, glycoluril, urea cyanurate, ammonium polyphosphate, and a condensation product of melamine from the series melem, melam, melon and/or a higher condensed compound or a reaction product of melamine with phosphoric acid or a mixture thereof.

Representative organohalogen flame retardants are, for example:

Polybrominated diphenyl oxide (DE-60F, Great Lakes Corp.), decabromodiphenyl oxide (DBDPO; Saytex® 102E), tris[3-bromo-2,2-bis(bromomethyl)propyl] phosphate (PB 370®, FMC Corp.), tris(2,3-dibromopropyl) phosphate, tris(2,3-dichloropropyl)phosphate, chlorendic acid, tetrachlorophthalic acid, tetrabromophthalic acid, polychloroethyl triphosphonate mixture, tetrabromobisphenol A bis(2,3-dibromopropyl ether) (PE68), brominated epoxy resin, ethylene-bis(tetrabromophthalimide) (Saytex® BT-93), bis(hexachlorocyclopentadieno)cyclooctane (Declorane Plus®), chlorinated paraffins, octabromodiphenyl ether, 1,2-bis(tribromophenoxy)ethane (FF680), tetrabromo-bisphenol A (Saytex® RB100), ethylene bis-(dibromo-norbornanedicarboximide) (Saytex® BN-451), bis-(hexachlorocyclopentadieno) cyclooctane, PTFE, tris-(2,3-dibromopropyl)-isocyanurate, and ethylene-bis-tetrabromophthalimide.

The organohalogen flame retardants mentioned above are routinely combined with an inorganic oxide synergist. Most common for this use are zinc or antimony oxides, e.g. $Sb_2O_3$ or $Sb_2O_5$. Boron compounds are suitable, too.

Representative inorganic flame retardants include, for example, aluminium trihydroxide (ATH), boehmite (AlOOH), magnesium dihydroxide (MDH), hydrotalcite, zinc borates, $CaCO_3$, (organically modified) layered silicates, (organically modified) layered double hydroxides, and mixtures thereof.

Particularly preferred as additional flame retardant are nitrogen generating compounds selected from the group consisting of melamine cyanurate, melamine polyphosphate, ammonium polyphosphate, melamine ammonium phosphate, melamine ammonium polyphosphate, melamine ammonium pyrophosphate, a condensation product of melamine with phosphoric acid and other reaction products of melamine with phosphoric acid and mixtures thereof.

The above-mentioned additional flame retardant classes are advantageously contained in the composition of the invention in an amount from about 0.5% to about 40.0% by weight of the organic polymer substrate; for instance about 1.0% to about 30.0%; for example about 2.0% to about 25.0% by weight based on the total weight of the composition.

The combination of the heptaphosphorus-derived ($P_7$) compound, as defined above, and the additional flame retardant is preferably contained in the flame retardant compositions in an amount from 0.5-60.0 wt. %, preferably 2.0-55.0 wt. %, based on the total weight of the composition.

According to another embodiment, the invention relates to flame retardant compositions which additionally comprise as additional component so-called anti-dripping agents.

These anti-dripping agents reduce the melt flow of the thermoplastic polymer and inhibit the formation of drops at high temperatures. Various references, such as U.S. Pat. No. 4,263,201, describe the addition of anti-dripping agents to flame retardant compositions.

Suitable additives that inhibit the formation of drops at high temperatures include glass fibres, polytetrafluoroethylene (PTFE), high temperature elastomers, carbon fibres, glass spheres and the like.

The addition of polysiloxanes of different structures has been proposed in various references; cf. U.S. Pat. Nos. 6,660,787, 6,727,302 or 6,730.720.

According to a further embodiment, the invention relates to flame retardant compositions which additionally comprise as additional components fillers and reinforcing agents. Suitable fillers are, for example, glass powder, glass microspheres, silica, mica and talcum.

Stabilizers are preferably halogen-free and selected from the group consisting of nitroxyl stabilizers, nitrone stabilizers, amine oxide stabilizers, benzofuranone stabilizers, phosphite and phosphonite stabilizers, quinone methide stabilizers and monoacrylate esters of 2,2'-alkylidenebisphenol stabilizers.

As mentioned above, the composition according to the invention may additionally contain one or more conventional additives, for example selected from pigments, dyes, plasticizers, antioxidants, thixotropic agents, levelling assistants, basic co-stabilizers, metal passivators, metal oxides, organophosphorus compounds, further light stabilizers and mixtures thereof, especially pigments, phenolic antioxidants, calcium stearate, zinc stearate, UV absorbers of the 2-hydroxy-benzophenone, 2-(2'-hydroxyphenyl)benzotriazole and/or 2-(2-hydroxyphenyl)-1,3,5-triazine groups.

Preferred additional additives for the compositions as defined above are processing stabilizers, such as the above-mentioned phosphites and phenolic antioxidants, and light stabilizers, such as benzotriazoles. Preferred specific antioxidants include octadecyl 3-(3,5-di-tert-butyl-4-hydroxyphenyl) propionate (IRGANOX 1076), pentaerythritoltetrakis[3-(3,5-di-tert-butyl-4-hydroxyphenyl) propionate] (IRGANOX 1010), tris(3,5-di-tert-butyl-4-hydroxyphenyl) isocyanurate (IRGANOX 3114), 1,3,5-trimethyl-2,4,6-tris (3,5-di-tert-butyl-4-hydroxybenzyl)benzene (IRGANOX 1330), triethyleneglycol-bis[3-(3-tert-butyl-4-hydroxy-5-methylphenyl) propionate] (IRGANOX 245), and N,N'-hexane-1,6-diyl-bis[3-(3,5-di-tert-butyl-4-hydroxyphenyl) propionamide] (IRGANOX 1098). Specific processing stabilizers include tris(2,4-di-tert-butylphenyl) phosphite (IRGAFOS 168), 3,9-bis(2,4-di-tert-butylphenoxy)-2,4,8,10-tetraoxa-3,9-diphosphaspiro[5.5]undecane (IRGAFOS 126), 2,2',2"-nitrilo[triethyl-tris(3,3',5,5'-tetra-tert-butyl-1, 1'-biphenyl-2,2'-diyl)] phosphite (IRGAFOS 12), and tetrakis(2,4-di-tert-butylphenyl)-[1,1-biphenyl]-4,4'-diylbisphosphonite (IRGAFOS PEPQ). Specific light stabilizers indude 2-(2H-benzotriazole-2-yl)-4,6-bis(1-methyl-1-phenylethyl)phenol (TINUVIN 234), 2-(5-chloro(2H)-benzotriazole-2-yl)-4-(methyl)-6-(tert-butyl)phenol (TINUVIN 326), 2-(2H-benzotriazole-2-yl)-4-(1,1,3,3-tetramethylbutyl)phenol (TINUVIN 329), 2-(2H-benzotriazole-2-yl)-4-

(tert-butyl)-6-(sec-butyl)phenol (TINUVIN 350), 2,2'-methylenebis(6-(2H-benzotriazol-2-yl)-4-(1,1,3,3-tetramethylbutyl)phenol) (TINUVIN 360), and 2-(4,6-diphenyl-1,3,5-triazin-2-yl)-5-[(hexyl)oxy]-phenol (TINUVIN 1577), 2-(2'-hydroxy-5'-methylphenyl)benzotriazole (TINUVIN P), 2-hydroxy-4-(octyloxy)benzophenone (CHI-MASSORB 81), 1,3-bis-[(2'-cyano-3',3'-diphenylacryloyl)oxy]-2,2-bis-{[(2'-cyano-3',3'-diphenylacryloyl)oxy]methyl}-propane (UVINUL 3030, BASF), ethyl-2-cyano-3,3-diphenylacrylate (UVINUL 3035, BASF), and (2-ethylhexyl)-2-cyano-3,3-diphenylacrylate (UVINUL 3039, BASF).

According to a further embodiment the compositions comprise as an optional component the additional flame retardants defined above and additives selected from the group consisting of polymer stabilizers and tetraalkylpiperidine derivatives.

Representative examples of tetraalkylpiperidine derivatives are selected from the group consisting of 1-Cyclohexyloxy-2,2,6,6-tetramethyl-4-octadecylaminopiperidine,
bis(1-Octyloxy-2,2,6,6-tetramethylpiperidin-4-yl) sebacate,
2,4-bis[(1-Cyclohexyloxy-2,2,6,6-tetramethylpiperidin-4-yl)butylamino]-6-(2-hy-droxyethylamino-s-triazine,
bis(1-Cyclohexyloxy-2,2,6,6-tetramethylpiperidin-4-yl) adipate,
2,4-bis[(1-Cyclohexyloxy-2,2,6,6-tetramethylpiperidin-4-yl)butylamino]-6-chloro-s-triazine,
1-(2-Hydroxy-2-methylpropoxy)-4-hydroxy-2,2,6,6-tetramethylpiperidine,
1-(2-Hydroxy-2-methylpropoxy)-4-oxo-2,2,6,6-tetramethylpiperidine,
1-(2-Hydroxy-2-methylpropoxy)-4-octadecanoyloxy-2,2,6,6-tetramethylpiperidine,
bis(1-(2-Hydroxy-2-methylpropoxy)-2,2,6,6-tetramethylpiperidin-4-yl) sebacate,
bis(1-(2-Hydroxy-2-methylpropoxy)-2,2,6,6-tetramethylpiperidin-4-yl) adipate,
2,4-bis{N-[1-(2-Hydroxy-2-methylpropoxy)-2,2,6,6-tetramethylpiperidin-4-yl]-N-butylamino}-6-(2-hydroxyethylamino))-s-triazine,
The reaction product of 2,4-bis[(1-cyclohexyloxy-2,2,6,6-tetramethylpiperidin-4-yl)butylamino]-6-chloro-s-triazine with N,N'-bis(3-aminopropyl)ethylenediamine),
2,4-bis[(1-Cyclohexyloxy-2,2,6,6-tetramethylpiperidin-4-yl)butylamino]-6-(2-hydroxyethylamino)-s-triazine,
The oligomeric compound which is the condensation product of 4,4'-hexamethylenebis(amino-2,2,6,6-tetramethylpiperidine) and 2,4-dichloro-6-[(1-cyclohexyloxy-2,2,6,6-tetramethylpiperidin-4-yl)butylamino]-s-triazine end-capped with 2-chloro-4,6-bis(dibutylamino)-s-triazine,
The compound of the formula And the compound of the formula in which n is from 1 to 15.

The additives mentioned above are preferably contained in an amount of 0.01 to 10.0%, especially 0.05 to 5.0%, relative to the weight of the polymer substrate of Component b).

The incorporation of the components defined above into the polymer component is carried out by known methods such as dry blending in the form of a powder, or wet mixing in the form of solutions, dispersions or suspensions for example in an inert solvent, water or oil. The additive components may be incorporated, for example, before or after molding or also by applying the dissolved or dispersed additive or additive mixture to the polymer material, with or without subsequent evaporation of the solvent or the suspension/dispersion agent. They may be added directly into the processing apparatus (e.g. extruders, internal mixers, etc.), e.g. as a dry mixture or powder, or as a solution or dispersion or suspension or melt.

The addition of the additive components to the polymer substrate can be carried out in customary mixing machines in which the polymer is melted and mixed with the additives. Suitable machines are known to those skilled in the art. They are predominantly mixers, kneaders and extruders.

The process is preferably carried out in an extruder by introducing the additive during processing.

Particularly preferred processing machines are single-screw extruders, contra-rotating and co-rotating twin-screw extruders, planetary-gear extruders, ring extruders or co-kneaders. Processing machines provided with at least one gas removal compartment can be used to which a vacuum can be applied.

Suitable extruders and kneaders are described, for example, in *Handbuch der Kunststoffextrusion*, Vol. 1 Grundlagen, Editors F. Henson, W. Knappe, H. Potente, 1989, pp. 3-7, ISBN:3-446-14339-4 (Vol. 2 *Extrusionsanlagen* 1986, ISBN 3-446-14329-7).

For example, the screw length is 1-60 screw diameters, preferably 35-48 screw diameters. The rotational speed of the screw is preferably 10-600 rotations per minute (rpm), preferably 25-300 rpm.

The maximum throughput is dependent on the screw diameter, the rotational speed and the driving force. The process of the present invention can also be carried out at a level lower than maximum throughput by varying the parameters mentioned or employing weighing machines delivering dosage amounts.

If a plurality of components is added, these can be premixed or added individually.

The additive components and optional further additives can also be added to the polymer in the form of a master batch)("concentrate") which contains the components in a concentration of, for example, about 2.0% to about 80.0% and preferably 5.0% to about 50.0% by weight incorporated in a polymer. The polymer is not necessarily of identical structure than the polymer where the additives are added finally. In such operations, the polymer can be used in the form of powder, granules, solutions, and suspensions or in the form of lattices.

The additive components optional further additives can also be added to the polymer in the form of a master batch ("concentrate") which contains the components in a concentration of, for example, about 1.0% to about 40.0% and preferably 2.0% to about 20.0% by weight incorporated in a polymer. The polymer is not necessarily of identical structure than the polymer where the additives are added finally. In such operations, the polymer can be used in the form of powder, granules, solutions, and suspensions or in the form of lattices.

Incorporation can take place prior to or during the shaping operation. The materials containing the additives of the invention described herein preferably are used for the production of molded articles, for example injection molded or roto-molded articles, injection molded articles, profiles and the like, and fibres, spun melt non-woven, films or foams.

The invention also relates to a heptaphosphorus-derived ($P_7$) compound selected from the group consisting of triazine heptaphosphide and trialkylheptaphosphine of the formula $$P_7(R_x)_3 \qquad (I),$$

Wherein $R_7$ represents a group of the partial formula $$—CR_1R_2R_3 \qquad (A),$$

Wherein
a) One of $R_1$, $R_2$ and $R_3$ represents hydrogen;
   One of $R_1$, $R_2$ and $R_3$ represents $C_1$-$C_4$-alkyl, phenyl or $C_1$-$C_4$-alkyl substituted by phenyl; and
   One of $R_1$, $R_2$ and $R_3$ represents the group of the partial formula $$—CH=CR_aR_b \qquad (B),$$

Wherein
   One of $R_a$ and $R_b$ represents $(C_1$-$C_4alkyl)_3silyl$; and the other
   One of $R_a$ and $R_b$ represents $C_1$-$C_4$-alkyl, phenyl or $C_1$-$C_4$-alkyl substituted by phenyl; or
b) One of $R_1$, $R_2$ and $R_3$ represents hydrogen;
   One of $R_1$, $R_2$ and $R_3$ represents $C_1$-$C_4$-alkyl, phenyl or $C_1$-$C_4$-alkyl substituted by phenyl; and
   One of $R_1$, $R_2$ and $R_3$ represents the group of the partial formula $$—CH—C(=O)—R_a \qquad (C),$$

Wherein
   $R_a$ represents $C_1$-$C_4$-alkyl, phenyl or $C_1$-$C_4$-alkyl substituted by phenyl; or
   Wherein
c) One of $R_1$, $R_2$ and $R_3$ represents hydroxy;
   One of $R_1$, $R_2$ and $R_3$ represents hydrogen; and
   One of $R_1$, $R_2$ and $R_3$ represents $C_1$-$C_4$-alkyl, phenyl or $C_1$-$C_4$-alkyl substituted by phenyl; or
d) One of $R_1$, $R_2$ and $R_3$ represents hydroxy; and
   two of $R_1$, $R_2$ and $R_3$ represent $C_1$-$C_4$-alkyl, phenyl or $C_1$-$C_4$-alkyl substituted by phenyl.

Triazine heptaphosphide and trialkylheptaphosphine (I) are obtainable by known and analogous methods.

A preferred method for preparing triazine heptaphosphide is the reaction of tris-trialkyl-silyl-heptaphosphine, e.g. $P_7(TMS)_3$ (=tris-trimethylsilyiheptaphosphine), by addition with 1-3 equivalents triazine, e.g. with melamine or a derivative thereof, such as the condensation product of melamine from the series melem, melam, melon and/or a higher condensed compound or the reaction product of melamine with phosphoric acid or a mixture thereof. This process is also subject matter of the invention and illustrated by the Examples.

The invention also relates to trimelamine heptaphosphide and to the preparation thereof.

The method for preparing trialkylheptaphosphine (I) depends on the structure of the alkyl substituent.

In the event that a compound (I) is desired, wherein $R_x$ represents a group of the partial formula $$—CR_1R_2R_3 \qquad (A),$$

Wherein
a) One of $R_1$, $R_2$ and $R_3$ represents hydrogen;
    One of $R_1$, $R_2$ and $R_3$ represents $C_1$-$C_4$-alkyl, phenyl or $C_1$-$C_4$-alkyl substituted by phenyl; and
    One of $R_1$, $R_2$ and $R_3$ represents the group of the partial formula $$—CH=CR_aR_b \quad (B),$$

Wherein
    One of $R_a$ and $R_b$ represents $(C_1$-$C_4$alkyl$)_3$silyl; and the other
    One of $R_a$ and $R_b$ represents $C_1$-$C_4$-alkyl, phenyl or $C_1$-$C_4$-alkyl substituted by phenyl; or
b) One of $R_1$, $R_2$ and $R_3$ represents hydrogen;
    One of $R_1$, $R_2$ and $R_3$ represents $C_1$-$C_4$-alkyl, phenyl or $C_1$-$C_4$-alkyl substituted by phenyl; and
    One of $R_1$, $R_2$ and $R_3$ represents the group of the partial formula $$—CH—C(=O)—R_a \quad (C),$$

Wherein
    $R_a$ represents $C_1$-$C_4$-alkyl, phenyl or $C_1$-$C_4$-alkyl substituted by phenyl;
the known starting material tris-trialkylsilyl-heptaphosphide, e.g. $P_7(TMS)_3$ (=tris-trimethylsilylheptaphosphide), is reacted by addition with at least 3 equivalents of a compound $$R_1—C(=O)—CH=CH—R_2 \quad (II),$$

Wherein $R_1$ and $R_2$ independently of one another represent $C_1$-$C_4$-alkyl, phenyl or $C_1$-$C_4$-alkyl substituted by phenyl (variant a));
and removing the trialkylsilyl, e.g. trimethylsilyl, group from the addition compound (variant b)).

In the event that 3 equivalents of chalcone (1,3-diphenyl-2-propen-1-on; $R_1$ and $R_2$=phenyl) are used as the starting material (II), a compound (I) is obtained, wherein in the partial formula (B), one of $R_a$ and $R_b$ represents $(C_1$-$C_4$alkyl$)_3$silyl (variant a)); and the other one of $R_a$ and $R_b$ represents phenyl. The subsequent removal of the silyl group produces a compound which may be defined as $P_7$(chalcone)$_3$ (variant b)).

This process is also subject matter of the invention and illustrated by the Examples.

In the event that according variant c) a compound (I) is desired, wherein $R_x$ represents a group of the partial formula $$—CR_1R_2R_3 \quad (A),$$

Wherein
    One of $R_1$, $R_2$ and $R_3$ represents hydroxy;
    One of $R_1$, $R_2$ and $R_3$ represents hydrogen; and
    One of $R_1$, $R_2$ and $R_3$ represents $C_1$-$C_4$-alkyl, phenyl or $C_1$-$C_4$-alkyl substituted by phenyl;
the known starting material tris-trialkylsilyl-heptaphosphide, e.g. $P_7(TMS)_3$ (=tris-trimethylsilylheptaphosphide), is reacted by addition with at least 3 equivalents of an aldehyde:

$$H—C(=O)—CR_1R_2R_3 \quad (III),$$

Wherein $R_1$, $R_2$ and $R_3$ independently of one another represent $C_1$-$C_4$-alkyl, phenyl or $C_1$-$C_4$-alkyl substituted by phenyl (variant c)).

The corresponding addition with a ketone (variant d)) produces an addition compound (I), wherein
d) One of $R_1$, $R_2$ and $R_3$ represents hydroxy; and
    two of $R_1$, $R_2$ and $R_3$ represent $C_1$-$C_4$-alkyl, phenyl or $C_1$-$C_4$-alkyl substituted by phenyl.

These process methods by analogous methods are also subject matter of the invention.

Another preferred embodiment of the invention relates to a heptaphosphorus-derived ($P_7$) compound selected from the group consisting of melamine heptaphosphide and trialkylheptaphosphine (I), wherein
    $R_x$ represents the group (A), wherein
    a) One of $R_1$, $R_2$ and $R_3$ represents hydrogen;
        One of $R_1$, $R_2$ and $R_3$ represents $C_1$-$C_4$-alkyl, phenyl or $C_1$-$C_4$-alkyl substituted by phenyl; and
        One of $R_1$, $R_2$ and $R_3$ represents the group (B), wherein
            One of $R_a$ and $R_b$ represents $(C_1$-$C_4$alkyl$)_3$silyl; and the other
            One of $R_a$ and $R_b$ represents $C_1$-$C_4$-alkyl, phenyl or $C_1$-$C_4$-alkyl substituted by phenyl; or
    b) One of $R_1$, $R_2$ and $R_3$ represents hydrogen;
        One of $R_1$, $R_2$ and $R_3$ represents $C_1$-$C_4$-alkyl, phenyl or $C_1$-$C_4$-alkyl substituted by phenyl; and
        One of $R_1$, $R_2$ and $R_3$ represents the group (C), wherein
            $R_a$ represents $C_1$-$C_4$-alkyl, phenyl or $C_1$-$C_4$-alkyl substituted by phenyl.

A particularly preferred embodiment of the invention is a trialkylheptaphosphine compound (I), wherein
    $R_x$ represents the group (A), wherein
    a) One of $R_1$, $R_2$ and $R_3$ represents hydrogen;
        One of $R_1$, $R_2$ and $R_3$ represents phenyl; and
        One of $R_1$, $R_2$ and $R_3$ represents the group (B), wherein
            One of $R_a$ and $R_b$ represents trimethylsilyl; and the other
            One of $R_a$ and $R_b$ represents phenyl; or
    b) One of $R_1$, $R_2$ and $R_3$ represents hydrogen;
        One of $R_1$, $R_2$ and $R_3$ represents phenyl; and
        One of $R_1$, $R_2$ and $R_3$ represents the group (C), wherein
            $R_a$ represents phenyl.

The preparation of these compounds is illustrated in the Examples.

The following Examples illustrate the invention:

EXAMPLES

Abbreviations
sec: second(s)
min: minute(s)
h: hours(s)
rpm: rotations per minute
IEC: International Electrotechnical Commission
ISO: International Organization for Standardization
TMS: Trimethylsilyl group
THF: Tetrahydrofuran
$P_7(TMS)_3$: tris-(Trimethylsilyl)-heptaphosphine
$P_7$(TMS-chalcone)$_3$: tris[1,3-diphenyl-3-(trimethylsilyloxy)-2-propenyl)]heptaphosphine
$P_7$(chalcone)$_3$: tris-1(1,3-diphenyl-3-oxopropyl)heptaphosphine Example 1 a) Preparation of tris(1,3-diphenyl-3-trimethylsilyloxy-2-propenyl)heptaphosphine from chalcone and $P_7TMS_3$ Dissolve 0.100 g (0.229 mmol) $P_7(TMS)_3$ (as obtained by the method described in H. Schmidbaur, A. Bauer, *An improved preparation of tris(trimethylsilyl)heptaphosphine, Phosphorus, Sulfur, and Silicon*, 1995, Vol. 102. pp. 217-219) in 3 ml THF and add drop-wise a THF solution of 0.143 g (0.687 mmol) 1,3-diphenyl-2-propen-1-one, [(E)-chalcone], Sigma Aldrich Co. LLC). Remove the THF under reduced pressure. Wash the residue with hexane and dry the light yellow powder under reduced pressure. Crystals suitable for single crystal x-ray diffraction are grown from a slowly evaporating THF solution of the title product ($P_7$(TMS-chalcone)$_3$). The product is obtained with a purity exceeding 95%.

Analytical Data
Elemental analysis [% found/% theory]: C: 61.52/61.20; H: 6.35/5.98; P: 19.88/20.43;
$^1$H NMR (THF-d8): 7.53-7.01 (m, 30H), 5.89-5.59 (m, 3H), 4.79-4.49 (m, 3H), 0.10 (s, 27H);
$^{31}$P NMR (THF-d8): 122.48-100.84 (m, 3P), 112.49-130.50 (m, 1P), 156.12-177.15 (m, 3P);
Raman [cm$^{-1}$]: 3057, 2956, 2897, 1634, 1596, 1487, 1445, 1404, 1342, 1310, 1277, 1212, 1186, 1154, 1094, 1021, 997, 903, 826, 764, 720, 685, 638, 605, 520, 472, 408, 387, 367, 346, 293, 272;
TGA Nitrogen: T5% mass loss: 221° C., T50% mass loss: 272° C.

b) Evaluation of $P_7$(TMS-Chalcone)$_3$ as a Flame Retardant in Polyurethane

The adduct $P_7$(TMS-chalcone)$_3$ is incorporated with the amounts indicated in Table 1 into thermoplastic polyurethane by melt extrusion with a double screw extruder that operates at 80 rpm and a temperature of 210° C. The residence time of the product is 3 min. Test bars with dimensions of 125 mm×13 mm×1.6 mm are prepared by injection molding with a pressure of 10 bar. Specimen are tested in the vertical flame test according to IEC 60695-11-20, with the limitation that only two test bars are used to obtain the after flame time. Samples of $P_7$(TMS-chalcone)$_3$ extinguish readily, as shown in Table 1.

TABLE 1

Polyurethane formulations and results of vertical flame test.

| | Amounts [% w/w] | |
|---|---|---|
| | 1 | 2 |
| Elastollan ® (BASF Polyurethanes GmbH) 1185 A10 | 100.0 | 96.4 |
| tris(1,3-Diphenyl-3-trimethylsilyloxy-2-propenyl)-heptaphosphine [=$P_7$(TMS-Chalcone)$_3$] | 0.0 | 3.6 |
| Classification IEC60695-11-20 | V-2 | V-0 |
| After-flame time t1 [s] | 1 | 2 |
| After-flame time t2 [s] | 1 | 1 |
| Cotton pad ignited | Yes | No |

Example 2 a) Preparation of tris-1(1,3-diphenyl-3-oxopropyl)heptaphosphine by Removal of silyl Group in $P_7$TMS-chalcone$_3$ In a 50 ml Schlenk flask, 0.250 g $P_7$(TMS-chalcone)$_3$ are combined with 0.250 g NH$_4$F (Sigma Aldrich Co. LLC). 15 ml acetonitrile are added under a flow of inert gas and stirred overnight. The acetonitrile is removed, and the residue taken into THF and filtered. THF is removed under reduced pressure and the residue mobilized with hexane. The light yellow powder $P_7$(chalcone)$_3$ is filtered and dried under reduced pressure.

Analytical Data
Elemental analysis [% found/% theory]: C: 63.74/63.99; H: 4.89/4.65; P: 25.69/25.67;
$^{31}$P NMR (THF-d$_8$): 139.48-105.12 (br.), 100.68-60.12 (br.), 60.53-33.04 (br.), 31.05-32.66 (br.);
MS (MALDI+): Predicted m/z=845.1135. Measured m/z=845.1134;
TGA Nitrogen: T5% mass loss: 204° C., T50% mass loss: 308° C.

b) Evaluation of tris-1-(1,3-diphenyl-3-oxopropyl)heptaphosphine as a Flame Retardant in Thermoset epoxy Isophoronediamine (3-aminomethyl-3,5,5-trimethylcyclohexylamine, BASF SE), a medium viscosity bisphenol-A epoxy resin (Epilox® (LEUNA-Harze GmbH) A 19-03) and $P_7$(chalcone)$_3$ are combined at room temperature in a 50 ml beaker with the amounts indicated in Table 2 and immediately mixed with a high-speed mixing system (Hauschild DAC 600) at 2000 rpm for 4 min. No temperature increase is observed during mixing. The mixtures are poured into a round aluminium dish with an inner diameter of 85 mm. The mixture is cured for 2 h at 80° C. and 3 h at 125° C. under reduced pressure (100 mbar). The procedure yields fully cured epoxy discs with a diameter of 85 mm and a thickness of approximately 4 mm.

TABLE 2

| Epoxy formulations | | |
|---|---|---|
| Components | Formulation 1 [g] | Formulation 2 [g] |
| Isophoronediamine | 4.67 | 4.67 |
| Epilox ( ®LEUNA-Harze GmbH) A 19-03 | 20.33 | 20.33 |
| $P_7$Chalcone$_3$ | 0 | 4.06 |

The flammability properties of the epoxy formulations according to Table 2 are tested with a cone calorimeter following the procedures of ISO-5660-1, with the exception of using a round-shaped specimen instead of a square specimen. The results are summarized in Table 3 and show that the heat release rate of the epoxy is strongly reduced by $P_7$chalcone$_3$.

TABLE 3

| Flammability properties according to ISO 5660-1 | | |
|---|---|---|
| Sample | 1 | 2 |
| Peak Heat Release Rate [kW m$^{-2}$] | 1940 | 655 |
| Maximum Average Rate of Heat Emission [kW m$^{-2}$] | 686 | 227 |
| Total Heat Release [MJ m$^{-2}$] | 106 | 79 |
| Residual mass [%] | 1.7 | 9.5 | c) Preparation of Transparent epoxy Plates with tris-1-(1,3-diphenyl-3-oxopropyl)heptaphosphine 2.3 g tris-1-(1,3-Diphenyl-3-oxopropyl)heptaphosphine are given to dimethylformamide (DMF, Sigma Aldrich Co. LLC) to prepare a 5% w/w solution of the heptaphosphine compound in DMF. 23.0 g of a medium viscosity bisphenol-A epoxy resin (Epilox® (LEUNA-Harze GmbH) A 19-03) are added and the solution is homogenized on a shaking table for 1 h. A clear solution is obtained. DMF is removed by storage under reduced pressure of 5 kPa for 16 h at a temperature of 100° C. The solution of tris-1-(1,3-diphenyl-3-oxopropyl)heptaphosphine in the epoxy resin remains fully transparent after removing DMF and cooling the solution to room temperature.

Figure 1:
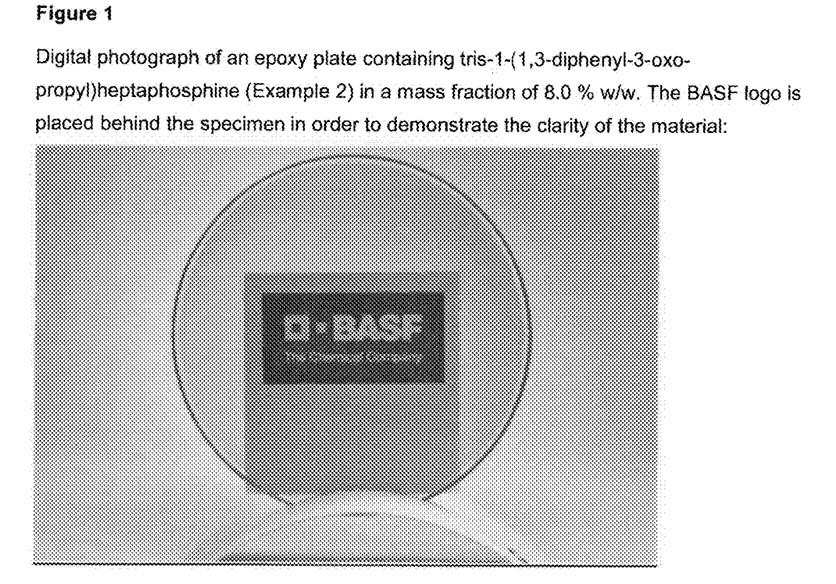
FIG. 1 illustrates a digital photograph of an epoxy plate containing tris-1-(1,3-diphenyl-3-oxo-propyl)heptaphosphine (Example 2) in a mass fraction of 8.0% w/w. The BASF logo is placed behind the specimen in order to demonstrate the clarity of the material.

3.0 g Triethylenetetramine (CAS No, 112-24-3, Sigma Aldrich Co. LLC) are added to 23.0 g of the solution of tris-1-(1,3-diphenyl-3-oxopropyl)heptaphosphine bisphenol-A epoxy resin and intensively mixed with a high-speed mixing system (Hauschild DAC 600) at 2000 rpm for 2 min. 22.0 g of the obtained mixture are poured into a flat aluminium dish with an inner diameter of 84 mm. The mixture is cured for 4 h at room temperature under atmospheric pressure and then cured for a further 2 h at a temperature of 120° C. under atmospheric pressure. A flat disc with a diameter of 84 mm is thus obtained. The sample is polished to a thickness of 3.1 mm in order to remove small bubbles from the surface. A digital photograph of the sample (FIG. 1) shows that a fully transparent material is obtained.

The flammability properties of the transparent epoxy plate containing 8.0% w/w of tris-1-(1,3-diphenyl-3-oxopropyl) heptaphosphine are tested with a cone calorimeter following the procedures of ISO-5660-1, with the exception of using a round-shaped specimen instead of a square specimen. The results are summarized in Table 4 and show that the heat release rate of the epoxy is strongly reduced by of tris-1-(1,3-diphenyl-3-oxopropyl)heptaphosphine.

TABLE 4

| Flammability properties according to ISO 5660-1 | |
| --- | --- |
| Sample | 1 |
| Peak Heat Release Rate [kW m$^{-2}$] | 720 |
| Maximum Average Rate of Heat Emission [kW m$^{-2}$] | 388 |
| Total Heat Release [MJ m$^{-2}$] | 64 |

Example 3 a) Preparation of the Decomposition Product of P$_7$(TMS)$_3$ in the Presence of Melamine (P$_7$Melamine Compound)

By choice of the molar ratios of the starting materials P$_7$(TMS)$_3$ and melamine, coordination polymers with different molar ratios of melamine can be obtained. In this example, the amount of the starting materials is chosen such that a ratio of melamine to P$_7$ of 1:1 is obtained in the final product. It is confirmed by observation of the characteristic vibrations in Raman spectroscopy that the P$_7$ cage remains intact in the final product.

A slurry of 0.100 g (0.802 mmol) melamine (Sigma Aldrich Co. LLC) in 4 ml methanol (124 mmol) is stirred, and 0.350 g (0.802 mmol) P$_7$(TMS)$_3$ dissolved in 3 ml toluene is added drop-wise. A yellow precipitate is formed within 30 min. The reaction mixture is stirred over night at 70° C. The mixture is filtered and the solid obtained is washed 2 times with 2 ml THF and dried for one hour under reduced pressure at 100° C.

Analytical Data

Elemental analysis [% found/% theory]: C: 12.5/10.4; N: 23.1/24.3; P: 57/62.7; Other: 7.4; Estimation for theoretical values: ratio of melamine to P$_7$ equals 1:1.

Raman [cm$^{-1}$]: 2242, 865, 738, 700, 656, 602, 505, 440, 405, 381, 351, 281;

TGA Nitrogen: T5% mass loss: 232° C., T50% mass loss: 417° C.

b) Evaluation of P$_7$ Melamine Compound as a Flame Retardant in Rigid Polyurethane Foam The P$_7$melamine compound is added to a polyether polyol with a viscosity of 2 Pa s (DIN 51 550) and OH-number of 400 mg KOH/g (DIN 53 240). A dispersion of the salt is obtained by stirring with a Lenart disc (Paul Vollrath GmbH & Co KG) at 1200 rpm for 2 min. Water, silicone surfactant, catalyst and blowing agent are added to the polyol blend and are homogenized by further stirring with the Lenart disc for 1 min at 1200 rpm. The isocyanate is added, and the mixture is immediately stirred with 1200 rpm for 10 sec. The reaction mixture is poured into a cardboard cup. The mixture expands immediately to form a cellular body with a multiple of the initial pour height. The same procedure is used to obtain a comparative example without a flame retardant (control). Concentrations indicated in Table 5 result in foam bodies with low densities of about 50 g l$^{-1}$ and a predominantly closed cell structure.

TABLE 5

| Polyurethane rigid foam formulation | |
| --- | --- |
| Components | Amount [g/100 g Polyol] |
| Polyether polyol ( ®Lupranol 3424, BASF Polyurethanes GmbH) | 100.00 |
| Surfactant Tegostab 8467 ( ®Evonik Industries AG) 8467 | 2.40 |
| Catalyst N,N-dimethylcyclohexylamine ( ®Lupragen N100, BASF SE) | 5.00 |
| Blowing agent cyclopentane (Cyclopentane PU 95%, TCI Europe N.V.) | 15.00 |
| Deionized water | 0.85 |
| Polymeric methylene diphenyl isocyanate ( ®Lupranat M20 S, BASF Polyurethanes GmbH) | 106.26 |
| P$_7$Melamine compound | 5.00 |

The flammability of the samples is tested in the vertical flame test according to Underwriters Laboratory standard 94 with the modification of the foam body being a round disc of 85 mm outer diameter and thickness of 20 mm. Flames are applied to the lower edge of the specimen. The results of the tests are reported in Table 6. The residual mass and the physical appearance of the residual samples after the burn test are also reported in Table 6. Addition of the P$_7$melamine compound results in extinction of the flame, and the foam core remains intact.

TABLE 6

| Flammability properties of rigid polyurethane foams | | |
| --- | --- | --- |
| Samples | 1 | 2 |
| Flame retardant | None | P$_7$Melamine salt |
| Amounts [g/100 g polyol] | — | 5 |
| After burn time 1 [sec] | ≥60 | 28 |
| After burn time 2 [sec] | — | 4 |
| Classification UL94 | none | V-1 |
| Residual mass [%] | 22 | 83 |
| Physical appearance | Hollow shell | Foam with burned surface layer |

Example 4 a) Preparation of the Decomposition Products, of $P_7(TMS)_3$ in the Presence of $ZnCl_2$ A solution of 0.19 g zinc dichloride (Sigma Aldrich Co. LLC) in THF is stirred and 0.2 g (0.458 mmol) $P_7(TMS)_3$ dissolved in 3 ml THF is added drop-wise. A yellow precipitate is formed immediately. The reaction mixture is stirred overnight at room temperature. The solid is filtered, washed with 2 ml THF and dried under reduced pressure.

Analytical Data

Elemental analysis [% found]: P 24.6; Si: 0.04; Zn: 26.6; Other: 48.8;

TGA Nitrogen: T5% mass loss: 405° C., T50% mass loss: ≥600° C.

b) Evaluation of the Decomposition Products of $P_7(TMS)_3$ in the Presence of $ZnCl_2$ as a Flame Retardant in Thermoplastic Polybutylene Terephthalate (PBT)

The zinc chloride heptaphosphide salt is incorporated in the amounts indicated in Table 7 into PBT by melt extrusion on a double screw extruder that operates at 80 rpm at a temperature of 260° C. The residence time of the product is 3 min. Test bars with dimensions of 125 mm×13 mm×1.6 mm are prepared by injection molding with a pressure of 10 bar. Specimen are tested in the vertical flame test according to IEC 60695-11-20, with the limitation that only two test bars are used to obtain the after-flame times. Samples containing the zinc chloride heptaphosphide compound extinguish readily, as shown in Table 7.

TABLE 7

Vertical flame test result of zinc chloride heptaphosphide salt.

| | Samples | |
|---|---|---|
| Components | 1 | 2 |
| Ultradur 4500 ( ®BASF SE) [% w/w] | 100.0 | 96.0 |
| Zinc chloride heptaphosphide salt | 0.0 | 4.0 |
| Classification IEC60695-11-20 | | V-2 |
| After-flame time t1 | ≥30 | 4 |
| After-flame time t2 | — | 12 |
| Cotton pad ignited | Yes | Yes |

Example 5 a) Preparation of tris(1-phenyl-3-trimethylsiloxy-2-propenyl)heptaphosohide from cinnamaldehyde and $P_7(TMS)_3$ $P_7(TMS)_3$ (4.00 g, 9.166 mmol) is dissolved in 20 ml THF in a Schlenk flask and cinnamaldehyde (3.63 g, 27.499 mmol) slowly added to the stirred solution. The solution is slightly warming up. The reaction mixture is stirred overnight and THF removed under reduced pressure to give tris(1-phenyl-3-trimethylsiloxy-2-propenyl)heptaphosphine. The product is obtained with a purity of 95%.

Analytical Data $^{31}$P NMR (THF-d8): 129.97-106.51 (m, 3P), −99.20-−130.50 (m, 1P), −149.28-−178.25 (m, 3P);

Elemental analysis [% found/theory]: C: 51.31/51.54; H:6.27/6.85; P: 25.95/25.85.

b) Preparation of tris(3-oxo-1-phenyl-propyl)heptaphosphine by Removal of silyl Group from tris(1-phenyl-3-trimethylsiloxy-2-propenyl)heptaphosphine 20 ml acetonitrile is added to tris(1-phenyl-3-trimethylsiloxy-2-propenyl)heptaphosphine prepared as decribed above, followed by 3.058 g (103.12 mmol) of $NH_4F$ (Sigma Aldrich Co. LLC). The reaction mixture is stirred overnight and the acetonitrile then decanted. 40 ml THF is added and the solution is washed with 2×20 ml degassed water to remove the $NH_4F$. The bright yellow solid is filtered on a glass frit and washed with 3×10 ml THF, followed by 3×10 ml diethyl ether. Volatiles are removed under reduced pressure overnight to yield a bright yellow powder. The desired product tris(3-oxo-1-phenyl-propyl)heptaphosphine is obtained with a purity of about 92%.

The obtained compound is easily subject to oligomerization and/or condensation reactions which makes purification for elemental analysis difficult. The desired structure is confirmed by MALDI-MS measurements.

Analytic Data

Elemental analysis [% found/theory]: C: 49.0/52.6; H:4.9/4.4; O: 8.0/7.8; P: 34.0/35.2;

TGA Nitrogen: T5% mass loss: 214° C., T50% mass loss: 352° C.;

MS (MALDI+): Predicted m/z=617.0196. Measured m/z=617.0198.

c) Evaluation of tris(3-oxo-1-phonyl-propyl)heptaphosphine as a Flame Retardent in Thermoset Epoxy Isophoronediamine, a medium viscosity bisphenol A epoxy resin (Epilox® (LEUNA-Harze GmbH) A 19-03) and tris-(3-oxo-1-phenyl-propyl)heptaphosphine are combined at room temperature in a 50 ml beaker in the amounts given in Table 8 and immediately mixed with a high-speed mixing system (Hauschild DAC 600) at 2000 rpm for 4 min. No temperature increase is observed during mixing. The mixtures are poured into a round aluminium dish with an inner diameter of 85 mm. The mixture is cured for 2 h at 80° C. and 3 h at 125° C. under reduced pressure (100 mbar). The procedure gives fully cured epoxy discs with a diameter of 85 mm and a thickness of approximately 4 mm.

TABLE 8

| Epoxy formulations | | |
|---|---|---|
| Components | Formulation 1 [g] | Formulation 2 [g] |
| Isophoronediamine | 4.67 | 4.67 |
| Epilox ( ®LEUNA-Harze GmbH) A 19-03 | 20.33 | 20.33 |
| Tris(3-oxo-1-phenylpropyl) heptaphosphine | 0 | 2.03 |

The flammability properties of the epoxy formulations according to Table 8 are tested with a cone calorimeter following the procedures of ISO-5660-1, with the variation of using a round specimen instead of a square disc. The results are summarized in Table 9 and show that the heat release rate of the epoxy is strongly reduced by tris(3-oxo-1-phenyl-propyl)heptaphosphine.

TABLE 9

Flammability properties according to ISO 5660-1

|  | 1 | 2 |
|---|---|---|
| Peak heat release rate [kW m$^{-2}$] | 1940 | 1009 |
| Maximum average rate of heat emission [kW m$^{-2}$] | 686 | 398 |
| Total heat release [MJ m$^{-2}$] | 106 | 81 |
| Residual mass [%] | 1.7 | 8.2 | d) Preparation of Transparent Expoxy Plates with tris(3-oxo-1-phenyl-propyl)heptaphosphine 2.3 g of tris(3-oxo-1-phenyl-propyl)heptaphosphine are given to dimethylformamide (DMF, Sigma Aldrich Co. LLC) to prepare a 5% w/w solution of the heptaphosphine compound in DMF. 23.0 g of a medium viscosity bisphenol-A epoxy resin (Epilox® (LEUNA-Harze GmbH) A 19-03) are added, and the solution is homogenized on a shaking table for 1 h. A clear solution is obtained. DMF is removed by storage under reduced pressure of 5 kPa for 16 h at a temperature of 100° C. The solution of tris-1-(1,3-diphenyl-3-oxopropyl)heptaphosphine in the epoxy resin remains fully transparent after removing DMF and cooling the solution to room temperature.

Figure 2:
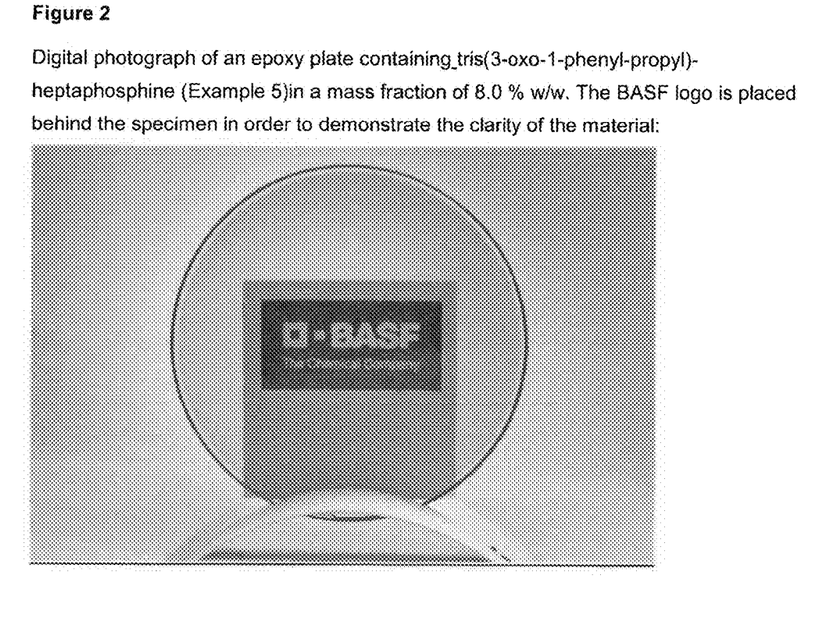
FIG. 2 illustrates a digital photograph of an epoxy plate containing tris(3-oxo-1-phenyl-propyl)-heptaphosphine (Example 5) in a mass fraction of 8.0% w/w. The BASF logo is placed behind the specimen in order to demonstrate the clarity of the material.

3.0 g Triethylenetetramine (CAS No. 112-24-3, Sigma Aldrich Co. LLC) are added to 23.0 g of the solution of tris(3-oxo-1-phenyl-propyl)heptaphosphine in the bisphenol-A epoxy resin and intensively mixed with a high-speed mixing system (Hauschild DAC 600) at 2000 rpm for 2 min. 22.0 g of the obtained mixture are poored into a flat aluminium dish with an inner diameter of 84 mm. The mixture is cured for 4 h at room temperature under atmospheric pressure and then cured for a further 2 h at a temperature of 120° C. under atmospheric pressure. A flat disc with a diameter of 84 mm is obtained. The sample is polished to a thickness of 3.3 mm in order to remove small bubbles from the surface. A digital photograph of the sample (FIG. 2) shows that a fully transparent material is obtained.

The flammability properties of the transparent epoxy plate containing 8.0% w/w tris(3-oxo-1-phenyl-propyl)heptaphosphine_are tested with a cone calorimeter following the procedures of ISO-5660-1, with the exception of using a round-shaped specimen instead of a square specimen. The results are summarized in Table 10 and show that the heat release rate of the epoxy is strongly reduced by tris(3-oxo-1-phenyl-propyl)heptaphosphine.

The comparison according to Example 5e) (see below) demonstrates that the flame retardant effect of tris(3-oxo-1-phenyl-propyl)heptaphosphine is comparable to the effect of red phosphorus when the same elemental concentration of phosphorus is used.

TABLE 10

Flammability properties according to ISO 5660-1

Figure 3:
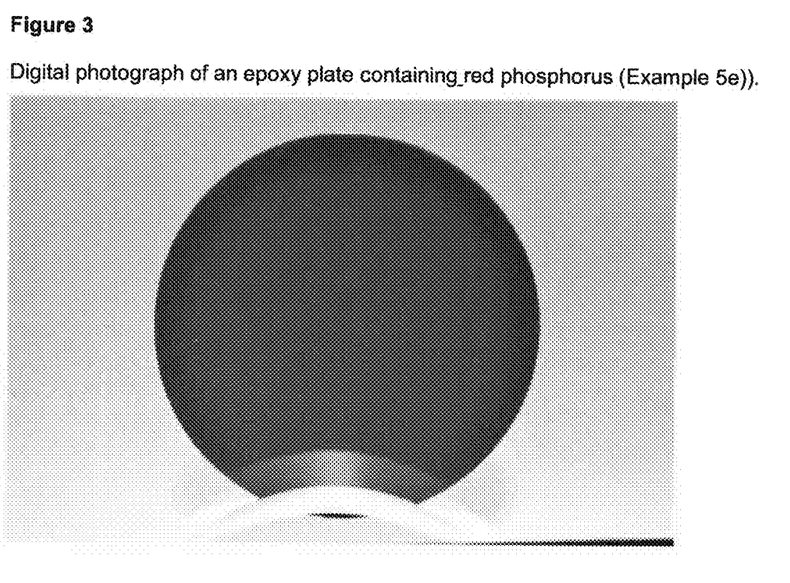
FIG. 3 illustrates a digital photograph of an epoxy plate containing red phosphorus (Example 5e).

| Sample | 1 |
|---|---|
| Peak Heat Release Rate [kW m$^{-2}$] | 808 |
| Maximum Average Rate of Heat Emission [kW m$^{-2}$] | 388 |
| Total Heat Release [MJ m$^{-2}$] | 59 | e) Comparative Example: Preparation of Epoxy Plates with Red Phosphorus 1.73 g red phosphorus paste (Exolit© RP 6520 available from Clariant SE) with an elemental concentration of phosphorus of 45% w/w are combined with 23.0 g medium viscosity bisphenol-A epoxy resin (Epilox® (LEUNA-Harze GmbH) A 19-03) and 3.0 g triethylenetetramine (CAS No. 112-24-3, Sigma Aldrich Co. LLC). The mixture is intensively mixed with a high-speed mixing system (Hauschild DAC 600) at 2000 rpm for 2 min. 22.0 g of the obtained mixture are poured into a flat aluminium dish with an inner diameter of 84 mm. The mixture is cured for 4 h at room temperature under atmospheric pressure and then cured for a further 2 h at a temperature of 120° C. under atmospheric pressure. A flat disc with a diameter of 84 mm is obtained. The sample is polished to a thickness of 3.4 mm in order to remove small bubbles from the surface. The material has an elemental concentration of phosphorus of 2.8% (w/w), which corresponds to the elemental concentration of phosphorus of the material described above (Example 5d)). A digital photograph of the sample is shown in FIG. 3.

The flammability properties of the epoxy plate containing red phosphorus are tested with a cone calorimeter following the procedures of ISO-5660-1, with the exception of using a round-shaped specimen instead of a square specimen. The results are summarized in Table 11.

TABLE 11

Flammability properties according to ISO 5660-1

| Sample | 1 |
|---|---|
| Peak Heat Release Rate [kW m$^{-2}$] | 868 |
| Maximum Average Rate of Heat Emission [kW m$^{-2}$] | 353 |
| Total Heat Release [MJ m$^{-2}$] | 53.4 |

The invention claimed is:

1. A composition, which comprises
   a) a heptaphosphorus-derived ($P_7$) compound selected from the group consisting of zinc heptaphosphorus halide, triazine heptaphosphide, tris-trialkylsilyl-heptaphosphide and trialkylheptaphosphine; and
   b) a polymer substrate.

2. The composition according to claim 1, which comprises a) the heptaphosphorus-derived ($P_7$) compound selected from the group consisting of zinc heptaphosphorus chloride, melamine heptaphosphide, tris-trimethylsilyl-heptaphosphide and trialkylheptaphosphine of the formula $$P_7(R_x)_3 \quad (I),$$

wherein $R_x$ represents a group of the partial formula $$-CR_1R_2R_3 \quad (A),$$

wherein
   a) one of $R_1$, $R_2$ and $R_3$ represents hydrogen;
   one of $R_1$, $R_2$ and $R_3$ represents $C_1$-$C_4$-alkyl, phenyl or $C_1$-$C_4$-alkyl substituted with phenyl; and
   one of $R_1$, $R_2$ and $R_3$ represents the group of the partial formula $$-CH=CR_aR_b \quad (B),$$

wherein
   one of $R_a$ and $R_b$ represents ($C_1$-$C_4$alkyl)$_3$silyl; and the other one of $R_a$ and $R_b$ represents $C_1$-$C_4$-alkyl, phenyl or $C_1$-$C_4$-alkyl substituted with phenyl; or
b) one of $R_1$, $R_2$ and $R_3$ represents hydrogen;
one of $R_1$, $R_2$ and $R_3$ represents $C_1$-$C_4$-alkyl, phenyl or $C_1$-$C_4$-alkyl substituted with phenyl; and
one of $R_1$, $R_2$ and $R_3$ represents the group of the partial formula —CH—C(=O)—$R_a$     (C), wherein
$R_a$ represents $C_1$-$C_4$-alkyl, phenyl or $C_1$-$C_4$-alkyl substituted with phenyl; or
wherein
c) one of $R_1$, $R_2$ and $R_3$ represents hydroxy;
one of $R_1$, $R_2$ and $R_3$ represents hydrogen; and
one of $R_1$, $R_2$ and $R_3$ represents $C_1$-$C_4$-alkyl, phenyl or $C_1$-$C_4$-alkyl substituted with phenyl; or
d) one of $R_1$, $R_2$ and $R_3$ represents hydroxy; and
two of $R_1$, $R_2$ and $R_3$ represent $C_1$-$C_4$-alkyl, phenyl or $C_1$-$C_4$-alkyl substituted with phenyl.

3. The composition according to claim 2, which comprises a) the heptaphosphorus-derived (P) compound selected from the group consisting of zinc heptaphosphorus chloride, melamine heptaphosphide, tris-trimethylsilyl-heptaphosphide and trialkylheptaphosphine (I), wherein
$R_x$ represents the group (A), wherein
a) one of $R_1$, $R_2$ and $R_3$ represents hydrogen;
one of $R_1$, $R_2$ and $R_3$ represents $C_1$-$C_4$-alkyl, phenyl or $C_1$-$C_4$-alkyl substituted with phenyl; and
one of $R_1$, $R_2$ and $R_3$ represents the group (B), wherein one of $R_a$ and $R_b$ represents ($C_1$-$C_4$alkyl)$_3$silyl; and the other
one of $R_a$ and $R_b$ represents $C_1$-$C_4$-alkyl, phenyl or $C_1$-$C_4$-alkyl substituted
with phenyl; or
b) one of $R_1$, $R_2$ and $R_3$ represents hydrogen;
one of $R_1$, $R_2$ and $R_3$ represents $C_1$-$C_4$-alkyl, phenyl or $C_1$-$C_4$-alkyl substituted with phenyl; and
one of $R_1$, $R_2$ and $R_3$ represents the group (C), wherein $R_a$ represents $C_1$-$C_4$-alkyl, phenyl or $C_1$-$C_4$-alkyl substituted with phenyl.

4. The composition according to claim 3, which comprises a) the heptaphosphorus-derived ($P_7$) compound selected from the group consisting of zinc heptaphosphorus chloride, melamine heptaphosphide, tris-trimethylsilyl-heptaphosphide and trialkylheptaphosphine (I), wherein
$R_x$ represents the group (A), wherein
a) one of $R_1$, $R_2$ and $R_3$ represents hydrogen;
one of $R_1$, $R_2$ and $R_3$ represents phenyl; and
one of $R_1$, $R_2$ and $R_3$ represents the group (B), wherein one of $R_a$ and $R_b$ represents trimethylsilyl; and the other one of $R_a$ and $R_b$ represents phenyl; or
b) one of $R_1$, $R_2$ and $R_3$ represents hydrogen;
one of $R_1$, $R_2$ and $R_3$ represents phenyl; and
one of $R_1$, $R_2$ and $R_3$ represents the group (C), wherein $R_a$ represents phenyl.

5. The composition according to claim 1, which comprises
a) the heptaphosphorus-derived ($P_7$) compound selected from the group consisting of zinc heptaphosphorus halide, triazine heptaphosphide, tris-trialkylsilyl-heptaphosphide and trialkylheptaphosphine; and
b') wherein the polymer substrate is a thermoplastic polymer substrate.

6. The composition according to claim 5, which comprises
a) the heptaphosphorus-derived ($P_7$) compound selected from the group consisting of zinc heptaphosphorus halide, triazine heptaphosphide, tris-trialkylsilyl-heptaphosphide and trialkylheptaphosphine; and
b") wherein the polymer substrate comprises a polyfunctional epoxide compound, and, optionally, a hardener compound.

7. The composition according to claim 1, which further comprises flame retardants and additives selected from the group consisting of tetraalkylpiperidine additives, polymer stabilizers, fillers and reinforcing agents.

8. The composition according to claim 7, which further comprises at least one additional flame retardant selected from the group consisting of phosphorus flame retardants, nitrogen generating flame retardants, organohalogen containing flame retardants and inorganic flame retardants.

9. The composition according to claim 8, wherein the additional flame retardant is a nitrogen containing compound selected from the group consisting of melamine cyanurate, melamine phosphate, melamine poly-phosphate, ammonium polyphosphate, melamine ammonium phosphate, melamine ammonium polyphosphate, melamine ammonium pyrophosphate, a condensation product of melamine with phosphoric acid and other reaction products of melamine with phosphoric acid and mixtures thereof.

10. The composition according to claim 8, wherein the additional flame retardant is a phosphorus containing flame retardant selected from the group consisting of tetra(2,6-dimethylphenyl)resorcinol diphosphate, salts of di-$C_1$-$C_4$alkylphosphinic acid, salts of hypophosphoric acid and 9,10-dihydro-9-oxa-10-phosphorylphenanthrene-10-oxide (DOPO) and its derivatives.

11. The composition according to claim 7, which additionally comprises at least one tetraalkylpiperidine derivative selected from the group consisting of
1-Cyclohexyloxy-2,2,6,6-tetramethyl-4-octadecylaminopiperidine,
bis(1-Octyloxy-2,2,6,6-tetramethylpiperidin-4-yl) sebacate,
2,4-bis[(1-Cyclohexyloxy-2,2,6,6-tetramethylpmeridin-4-yl)butylamino]-6-(2-hydroxy-ethylamino-s-triazine,
bis(1-Cyclohexyloxy-2,2,6,6-tetramethylpiperidin-4-yl) adipate,
2,4-bis[(1-Cyclohexyloxy-2,2,6,6-tetramethylpiperidin-4-yl)butylamino]-6-chloro-s-triazine,
1-(2-Hydroxy-2-methylpropoxy)-4-hydroxy-2,2,6,6-tetramethylpiperidine,
1-(2-Hydroxy-2-methylpropoxy)-4-oxo-2,2,6,6-tetramethylpiperidine,
1-(2-Hydroxy-2-methylpropoxy)-4-octadecanoyloxy-2,2,6,6-tetramethylpiperidine,
bis(1-(2-Hydroxy-2-methylpropoxy)-2,2,6,6-tetramethyl-piperidin-4-yl) sebacate,
bis(1-(2-Hydroxy-2-methylpropoxy)-2,2,6,6-tetramethyl-piperidin-4-yl) adipate,
2,4-bis {N-[1-(2-Hydroxy-2-methylpropoxy)-2,2,6,6-tetramethylpiperidin-4-yl]-N-butylamino}-6-(2-hydroxyethylamino)-s-triazine,
the reaction product of 2,4-bis[(1-cyclohexyloxy-2,2,6,6-tetramethylpiperidin-4-yl)-butylamino]-6-chloro-s-triazine with N,N'-bis(3-aminopropyl)ethylenediamine),
2,4-bis[(1-Cyclohexyloxy-2,2,6,6-tetramethylpiperidin-4-yl)butylamino]-6-(2-hydroxy-ethylamino)-s-triazine,
the oligomeric compound which is the condensation product of 4,4'-hexamethylene-bis(amino-2,2,6,6-tetramethylpiperidine) and 2,4-dichloro-6-[(1-cyclohexyloxy-2,2,6,6-tetramethylpiperidin-4-yl)butylamino]-s-triazine end-capped with 2-chloro-4,6-bis(dibutylamino)-s-triazine,
the compound of the formula and the compound of the formula in which n is from 1 to 15.

12. A process for inducing flame retardancy in polymers, which comprises adding to a polymer substrate a heptaphosphorus-derived ($P_7$) compound selected from the group consisting of zinc heptaphosphorus halide, triazine heptaphosphide, tris-trialkylsilyl-heptaphosphide and trialkylheptaphosphine.

13. A heptaphosphorus-derived ($P_7$) compound selected from the group consisting of triazine heptaphosphide and trialkylheptaphosphine of the formula $$P_7(R_x)_3 \qquad (I),$$

wherein $R_x$ represents a group of the partial formula $$-CR_1R_2R_3 \qquad (A),$$

wherein
a) one of $R_1$, $R_2$ and $R_3$ represents hydrogen;
   one of $R_1$, $R_2$ and $R_3$ represents $C_1$-$C_4$-alkyl, phenyl or $C_1$-$C_4$-alkyl substituted with phenyl; and
   one of $R_1$, $R_2$ and $R_3$ represents the group of the partial formula $$-CH=CR_aR_b \qquad (B),$$

wherein
   one of $R_a$ and $R_b$ represents ($C_1$-$C_4$alkyl)$_3$silyl; and the other
   one of $R_a$ and $R_b$ represents $C_1$-$C_4$-alkyl, phenyl or $C_1$-$C_4$-alkyl substituted with phenyl; or
b) one of $R_1$, $R_2$ and $R_3$ represents hydrogen;
   one of $R_1$, $R_2$ and $R_3$ represents $C_1$-$C_4$-alkyl, phenyl or $C_1$-$C_4$-alkyl substituted with phenyl; and
   one of $R_1$, $R_2$ and $R_3$ represents the group of the partial formula $$-CH-C(=O)-R_a \qquad (C),$$

wherein
   $R_a$ represents $C_1$-$C_4$-alkyl, phenyl or $C_1$-$C_4$-alkyl substituted with phenyl; or wherein
c) one of $R_1$, $R_2$ and $R_3$ represents hydroxy;
   one of $R_1$, $R_2$ and $R_3$ represents hydrogen; and
   one of $R_1$, $R_2$ and $R_3$ represents $C_1$-$C_4$-alkyl, phenyl or $C_1$-$C_4$-alkyl substituted with phenyl; or
d) one of $R_1$, $R_2$ and $R_3$ represents hydroxy; and
   two of $R_1$, $R_2$ and $R_3$ represent $C_1$-$C_4$-alkyl, phenyl or $C_1$-$C_4$-alkyl substituted with phenyl.

14. The heptaphosphorus-derived ($P_7$) compound according to claim 13 wherein $R_x$ represents the group (A), wherein
a) one of $R_1$, $R_2$ and $R_3$ represents hydrogen;
one of $R_1$, $R_2$ and $R_3$ represents $C_1$-$C_4$-alkyl, phenyl or $C_1$-$C_4$-alkyl substituted with phenyl; and
one of $R_1$, $R_2$ and $R_3$ represents the group (B), wherein
one of Ra and Rb represents (C1-C4alkyl)3silyl; and the other
one of Ra and Rb represents C1-C4-alkyl, phenyl or C1-C4-alkyl substituted with phenyl; or
b) one of $R_1$, $R_2$ and $R_3$ represents hydrogen;
one of $R_1$, $R_2$ and $R_3$ represents $C_1$-$C_4$-alkyl, phenyl or $C_1$-$C_4$-alkyl substituted with phenyl; and
one of $R_1$, $R_2$ and $R_3$ represents the group (C), wherein $R_a$ represents $C_1$-$C_4$-alkyl, phenyl or $C_1$-$C_4$-alkyl substituted with phenyl.

15. The heptaphosphorus-derived ($P_7$) compound according to claim 13 wherein the heptaphosphorus-derived ($P_7$) compound is trimelamine heptaphosphide.

16. The heptaphosphorus-derived ($P_7$) compound according to claim 13, wherein the compound is a trialkylheptaphosphine compound (I) and
$R_x$ represents the group (A), wherein
a) one of $R_1$, $R_2$ and $R_3$ represents hydrogen;
one of $R_1$, $R_2$ and $R_3$ represents phenyl; and
one of $R_1$, $R_2$ and $R_3$ represents the group (B), wherein
one of $R_a$ and $R_b$ represents trimethylsilyl; and the other
one of $R_a$ and $R_b$ represents phenyl; or
b) one of $R_1$, $R_2$ and $R_3$ represents hydrogen;
one of $R_1$, $R_2$ and $R_3$ represents phenyl; and
one of $R_1$, $R_2$ and $R_3$ represents the group (C), wherein $R_a$ represents phenyl.

* * * * *